United States Patent
Chin

(10) Patent No.: US 7,184,143 B2
(45) Date of Patent: Feb. 27, 2007

(54) METHOD FOR REMOTE SENSING OF POLLUTANT MOLECULES IN A TRANSPARENT MEDIUM USING ULTRA-SHORT INTENSE LASERS

(75) Inventor: See Leang Chin, Ste-Foy (CA)

(73) Assignee: Université Laval, Sainte-Foy (CA)

( * ) Notice: Subject to any disclaimer, the term of this patent is extended or adjusted under 35 U.S.C. 154(b) by 522 days.

(21) Appl. No.: 10/682,365

(22) Filed: Oct. 10, 2003

(65) Prior Publication Data
US 2004/0135998 A1    Jul. 15, 2004

Related U.S. Application Data

(60) Provisional application No. 60/417,648, filed on Oct. 11, 2002.

(51) Int. Cl.
*G01J 3/30* (2006.01)
(52) U.S. Cl. ....................................... 356/318
(58) Field of Classification Search ............. None
See application file for complete search history.

(56) References Cited

U.S. PATENT DOCUMENTS

2003/0123051 A1 *  7/2003  McGrew ................ 356/72

OTHER PUBLICATIONS

Remote Sensing of the Atmosphere Using Ultrashort Laser Pulses, Invs.: P. Rairoux et al. Appl. Phys. 2000, B71, pp. 573-580.
Exploring the Atmosphere With Lidars, Dept. of Physics and Astronomy, Professor R. Sica, The University of Western Ontario, CA N6A 3K7; Oct. 3, 2002, pp. 1-29.
LIDAR Tutorial, NASA US Government, Sparcle Announcement, Oct. 3, 2002, pp. 1 and 2.
LIDAR Tutorial (More on LIDAR), NASA US Government, Sparcle Announcement, Oct. 3, 2002, pp. 1-3.

* cited by examiner

*Primary Examiner*—Tu T. Nguyen
(74) *Attorney, Agent, or Firm*—Ogilvy Renault LLP

(57) ABSTRACT

There is described a method for identifying at least one molecule in a substantially transparent medium, the method comprising: transmitting high-power, ultra-short laser pulses into the medium so as to generate filaments in which a spontaneous fluorescence signal propagating along an axis of the filament is amplified by stimulated emission; detecting the amplified spontaneous fluorescence signal; and analyzing the florescence signal to identify said molecule.

10 Claims, 5 Drawing Sheets

METHOD FOR REMOTE SENSING OF POLLUTANT MOLECULES IN A TRANSPARENT MEDIUM USING ULTRA-SHORT INTENSE LASERS

CROSS-REFERENCE TO RELATED APPLICATIONS

The present application claims priority of U.S. provisional application No. 60/417,648, filed on Oct. 11, 2002.

FIELD OF THE INVENTION

The invention relates to the field of Light Detecting and Ranging (LIDAR). More specifically, it relates to identifying molecules in a transparent medium such as air.

BACKGROUND OF THE INVENTION

Filaments over distances up to several kilometers are formed when high-power ultra-short laser pulses are launched in air. They are created by a dynamic interplay between two nonlinear effects, i.e. Kerr self-focusing and subsequent plasma defocusing. Self-phase modulation and self-steepening of the pulse give rise to a strong broadening of the spectrum. The consequence is a white light laser pulse (super continuum). Potential practical applications of these phenomena include lightning discharge control and remote sensing.

It is known in the art to combine LIDAR (Light Detection and Ranging) techniques and time-resolved absorption spectroscopy techniques and apply them to a pulsed broadband light source in order to perform range-resolved multi-trace analyses simultaneously. While this process can be applied to the remote sensing of pollutants in the atmosphere, sensitivity is an issue. Normally, for detecting different pollutant molecules, different lasers with different output wavelengths are required. This causes difficulties especially for the analysis of multi-component mixtures.

There is a need to develop a new scheme of LIDAR technique to detect pollutant molecules in air, or any other transparent medium, with improved sensitivity.

SUMMARY OF THE INVENTION

Accordingly, an object of the present invention is to determine the composition of a transparent medium such as air or water using an efficient and simple remote sensing method.

It is also an object of the present invention to observe an amplification of an emitted signal in order to increase sensitivity in the remote sensing of molecules.

According to a first broad aspect of the present invention, there is provided a method for identifying at least one molecule in a substantially transparent medium, the method comprising: transmitting high-power, ultra-short laser pulses into the medium so as to generate filaments in which a spontaneous fluorescence signal propagating along an axis of the filament is amplified by stimulated emission; detecting the amplified spontaneous fluorescence signal; and analyzing the florescence signal to identify said molecule.

Preferably, the amplified spontaneous fluorescence signals are detected in a direction opposite that of the transmitted laser pulses and the detector is gated. Also preferably, transmitting comprises transmitting femtosecond laser pulses and transmitting is done using a terawatt femtosecond Ti-sapphire laser system.

Additionally, by using trigger-and-delay electronics, a fluorescence spectrum of the signal can be acquired at any given time corresponding to the sum of travel time of the laser to a given point in space and the travel time of the fluorescence signal from the point in space to the detector. By varying the delay between the firing of the laser and the acquisition of the spectrum, information on the composition of the medium as a function of the distance from the laser can be obtained.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

When high-power ultra-short (femtosecond) laser pulses are launched in air, they self-transform into streaks of filaments over distances up to several km. That is to say, multiple filaments of shorter lengths are substantially aligned in a non-continuous manner over distances up to several km. Although multiple filaments are common, it is not impossible that a single filament be created. These filaments are the result of a dynamic balance between two nonlinear effects. The first is self-focusing of a laser pulse due to the Kerr effect in the atmosphere. The beam focuses by itself, resulting in a small beam diameter and hence high peak intensity. At that self-focal region, the high intensity laser pulse induces multiphoton/tunnel ionization (MPI) of the gas molecules in air. This results in the weak plasma in the self-focal region, whose density is low (about $10^{15}/cm^3$) compared with the density of one atmosphere of air ($3\times10^{19}/cm^3$). The second balancing effect is the defocusing of the laser pulse in the weak plasma created in the self-focal region. The laser peak intensity in the filaments in air is clamped down to about $5\times10^{13}$ W/cm$^2$. At this intensity, most molecules will undergo MPI and fragmentation. Many of the ionization and fragmentation are expected to fluoresce with distinguishable molecular spectra due to the different nonlinear interaction between the molecules and the intense femtosecond laser fields. This nonlinear fluorescence created in the filament is a new physical phenomenon and is strongly emitted along the forward and backward directions. Since every molecule has its particular feature in the fluorescence spectrum, it is expected that these fluorescence spectra can be made use of as the fingerprint patterns for pollution measurement using the LIDAR technique.

The white light laser pulse (super continuum) combined with linear absorption spectroscopy technique has been used for atmospheric remote sensing. A terawatt femtosecond Ti-sapphire laser system mounted on a mobile unit, teramobile, was recently built to carry out long-range propagation experiments in air and LIDAR type of measurements in the atmosphere.

Figure 1:
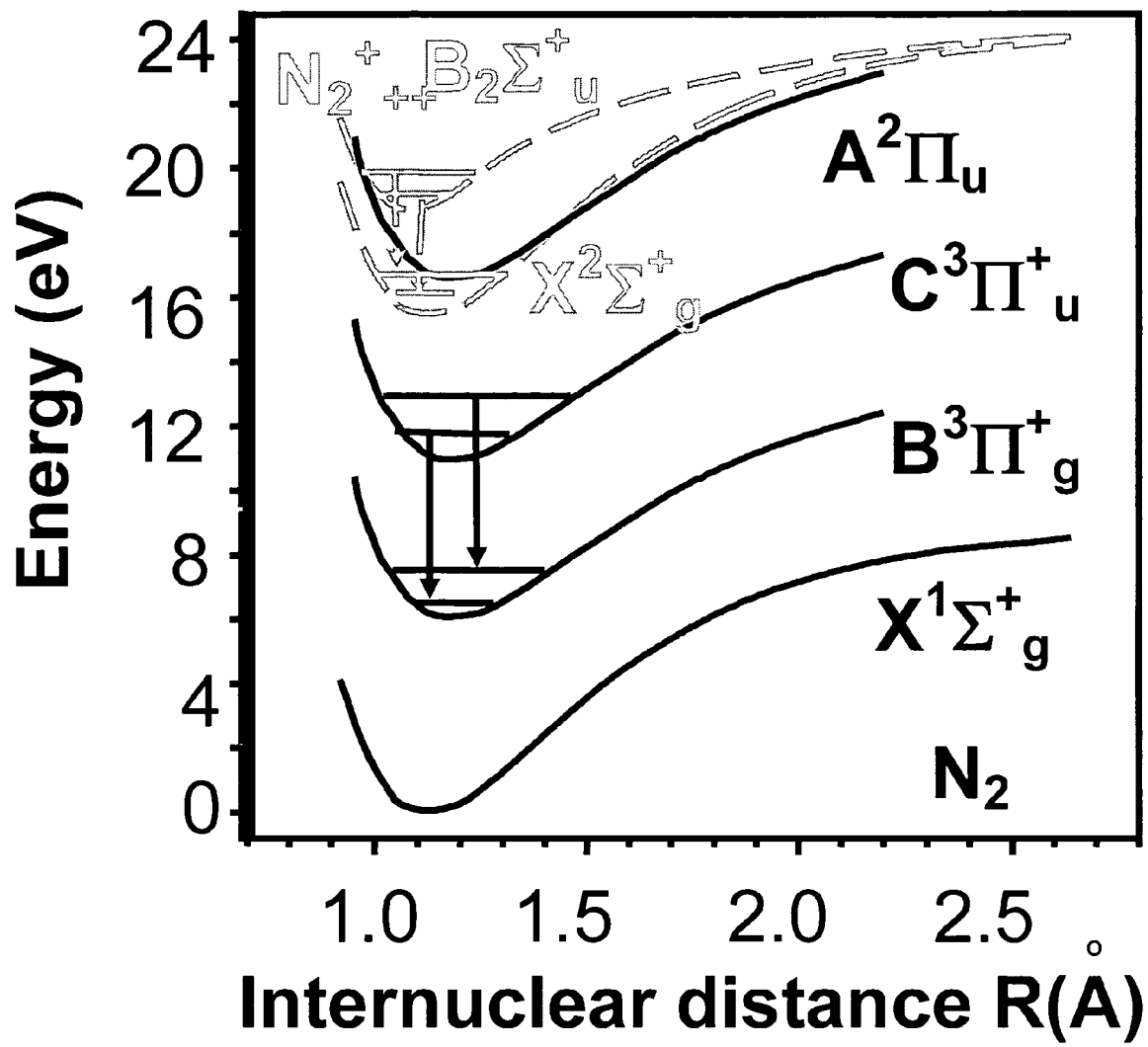
FIG. 1 is the potential energy curve for $N_2$ and $N_2^+$.

In air, so-called clean fluorescence of nitrogen molecules and ions are observed from the filaments; i.e. the contribution of the super continuum is quite low compared with that from the optical break down measured with long pulses. The spectra are assigned to the first negative band of $N_2^+$ ($B^2\Sigma_u^+ \to X^2\Sigma_g^-$) and the second positive band of $N_2$ ($C^3\pi_u \to B^3\pi_g$). We have proven that nitrogen molecules inside the filament are first ionized, some of them into the excited ionic state through the ejection of an inner valence electron. Subsequent radiative decay of the excited ion gives rise to the first negative band (See FIG. 1). Electron-ion recombination and collision lead to the emission of the second positive band. We investigated the fluorescence from inside the filaments generated by a femtosecond Ti-sapphire laser pulse in air. The angular distribution and intensity dependence of the signal show clear evidences of amplified spontaneous emission (ASE).

Strictly speaking, a filament is the weak plasma column left behind by the continuous series of self-foci of the laser pulse. The laser peak intensity inside the series of foci is clamped down to about $5\times10^{13}$ W/cm$^2$ in air.

The high power femtosecond laser system consists of a Ti:Sapphire oscillator (Spectra Physics Maitai) followed by a regenerative (Spectra Physics Spitfire) and a two-pass Ti:Sapphire amplifiers. The amplified beam is sent to a portable compressor that can be moved close to the experimental set-up. The pulse duration at the output of the compressor is 42 fs measured by a single-shot autocorrelator and the central wavelength is 810 nm with a bandwidth of 23 nm (FWHM). The maximum output energy is about 20 mJ per pulse with the repetition rate of 10 Hz.

Figure 2:
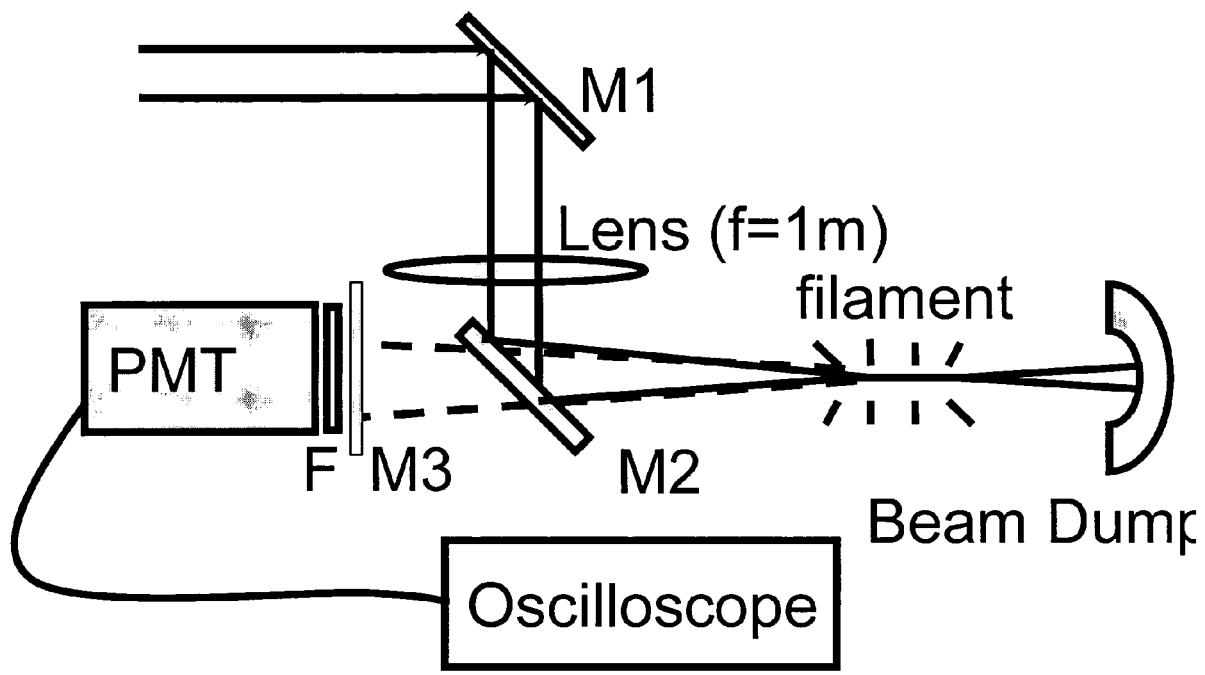
FIG. 2 is the setup used as an experimental setup.

The experimental setup is shown in FIG. 2(a) for analyzing fluorescence emission amplified by stimulated emission in a direction of the axis of the filament. The laser beam is firstly focused with an f=100 cm lens. A dielectric mirror (diameter=2.54 cm) having high reflectivity around 800 nm while transmitting UV light is put just after the lens to reflect the beam at a 45° incident angle. In the forward direction of the laser, filaments are generated before the geometrical focus. A beam dump blocks the laser beam just before the wall of the lab. The amplified fluorescence from air is detected using a photo multiplied tube (PMT) (Hamamatsu R74000U) which is put behind the last mirror facing the direction of the beam. An iris (5 mm diameter) is put in front of the PMT to limit the field of view. The fluorescence is selected by an appropriate interference filter with 10 nm bandwidth around the detected wavelength together with a high reflectivity dielectric coated fused silica mirror (reflectivity: 99%, central wavelength: 800; bandwidth: around 100 nm) a broad band filter in 800 nm for cutting off scattered laser light. The fluorescence studied includes (1-0) transition of the second positive band system of $N_2$ ($C^3\pi_u - B^3\pi_g$ transition) at 357 nm and the band head of the first negative band system of $N_2^+(B^2\Sigma_u^+ - X^2\Sigma_g^-$ transition) at 391 nm.

The experiment is also done without focusing lens. In this case, filaments are generated only due to self-focusing. The distance between the exit of compressor and the beam dump is about 13.5 m. Since the filament is far away from the detector, the fluorescence signals are much weaker than that in the focusing geometry. We use UV filter to cut the light above 400 nm instead of using interference filter to obtain more dynamics range for the signal. Thus the fluorescence signal from $N_2$ molecules and ions are all measured.

When the intense laser beam is focused by an external focusing lens, the filament will start before the geometrical focus and the filament length will increase towards the focusing lens with increasing laser energy. The intensity of the amplified fluorescence is found to increase nonlinearly with increasing pump laser energy. The latter is converted into filament length defined approximately as the distance between the geometrical focus and the position of the self-focus of the peak of the pulse (see below for more precision). Without external focusing lens, a parallel beam with a Gaussian beam profile will self-focus at:

$$z_f = \frac{0.367ka^2}{\left\{\left[\left(\frac{P}{P_{crit}}\right)^{1/2} - 0.852\right]^2 - 0.0219\right\}^{1/2}} \quad (1)$$

Here $ka^2$ indicates the diffraction length, where k is the wave number and a is the radius at $1/e^2$ level of the beam profile. In our experiment, the radius of the beam is around 5 mm. The critical power for self-focusing is:

$$P_{crit} = \frac{3.77\lambda^2}{8\pi n_0 n_2}$$

where $\lambda$ is the laser wavelength, $n_o$ and $n_2$ characterize the intensity dependent refractive indices $n=n_0+n_2 I$, where I is the laser intensity. In air, the critical power for self-focusing is 3 GW. In the case of external focusing using a lens of focal length f the position of the self-focus will change to:

The filament length $$z_f' = \frac{z_f f}{z_f + f} \text{ is } L = f - z_f'. \quad (2)$$

Any refocusing after the geometrical focus is neglected because the intensity would be weaker in the re-focusing zone and hence the fluorescence signal is weaker and is neglected as an approximation. The intensity of the fluorescence signal from $N_2$ at 357 nm collected by the fused silica lens versus the filament length is plotted in FIG. 3.

Figure 3:
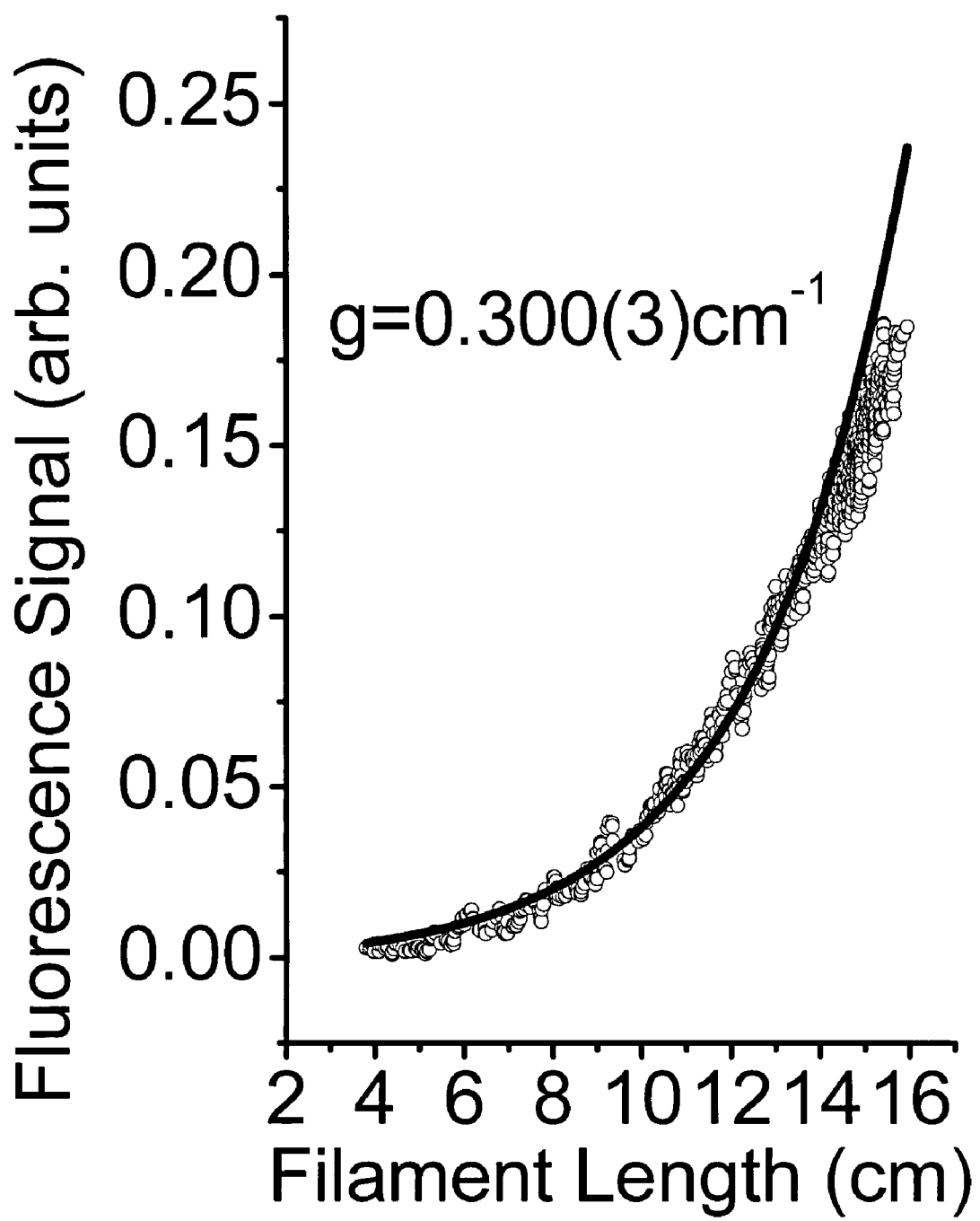
FIG. 3 is a graph of the fluorescence intensity of $N_2$ at 357 nm versus the filament length.

Consider the filament as a long slender line source emitting fluorescence and any small length as a point source, the spontaneous emission power going out into all directions from this point source is identical. Assuming that spontaneous emission occurs uniformly along the filament, the signal we detect in PMT for ASE is given by:

$$I \propto P = \int_0^L P_s e^{gl} dl + \text{Const.} = \frac{P_s}{g}(e^{gL} - 1). \quad (3)$$

$$= \begin{cases} \frac{P_s}{g}(e^{gL} - 1) \text{ (without amplification)} & (a) \\ \frac{P_s}{g} \cdot gL = P_s L \text{ (without amplification } g \to 0) & (b) \end{cases}$$

where $P_s$ is the spontaneous emission power per unit length which goes back along the filament, g is the optical gain coefficient, L is the filament length. In the case without amplification the total signal we detected is the sum of the emission power going into a certain solid angle from all the point sources along the filament. The total signal should thus be proportional to the filament length. However, the plot in FIG. 3 shows an exponential increase in the fluorescence signal with the filament length. This is a direct indication of the existence of gain. As shown in the FIG. 3, a calculated gain curve (solid line) by using $P_s$ and g as fitting parameters fits very well the measured data with a gain coefficient of 0.305 cm$^{-1}$. For the longer filament length, the experiment data are lower than that of calculated gain which is due to the saturation effect.

The fluorescence from the first negative band system of $N_2^+$ ($B^2\Sigma_u^+ - X^2\Sigma_g^-$ transition) at 391 nm are also studied. The fluorescence signal shows a similar tendency of exponential increase with filament length. It means the fluorescence from ions is also amplified. The gain coefficient is 0.34 cm$^{-1}$.

Figure 4:
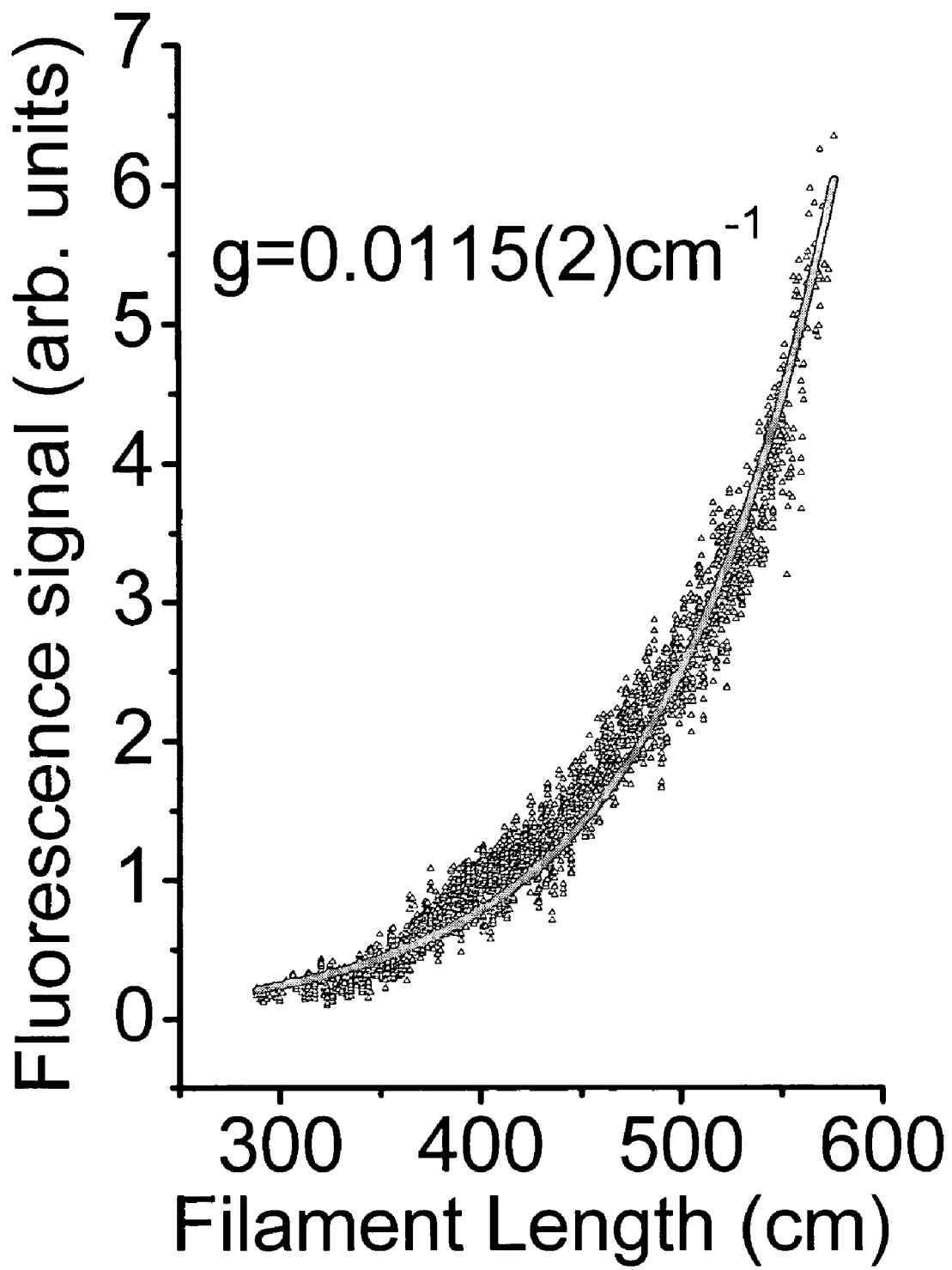
FIG. 4 is a graph of the fluorescence intensity of $N_2$ at 357 nm versus the filament length when the laser beam propagates in air without external focusing lens.

To study the long-distance case, we measured the intensity dependence of the fluorescence emission amplified by stimulated emission in a direction of the axis of the filament generated during the laser pulse free propagation in air. In this case, the laser beam is sent to air without any focusing lenses and the filaments are generated only due to self-focus. The starting point moves towards to the compressor and the filament becomes longer as the input laser energy increases. The filament length is limited by the confine of the lab. In this measurement, the filament length is determined by taking the distance between the beginning of the self-focusing point and the wall of lab, i.e. $L=1350-z_{71}'$ (cm). As we showed above, the fluorescence from both the neutral molecules and ions shows the existence of gain. Thus we expect that the signal in this measurement will show gain also. FIG. 4 is the plot for the fluorescence signal from nitrogen versus the filament length. The curve shows a similar tendency as that taken with an external focusing lens. The solid line shown in the figure is the fitting curve using Eq.4(a). The gain coefficient is around 0.0116 cm$^{-1}$.

When the $N_2$ molecules interact with the intense ultra fast field, the molecules will first go through multiple photon ionization. An inner-valence electron is ionized resulting in an electronically excited molecular ion. The recombination of the electrons and the ions in excited states generate the $N_2$ molecules in the continuum. The $N_2$ molecules will relax from the continuum down to electronic states. When the molecules go through radiative excited state, the fluorescence is emitted. Since the population of the states is created from the higher states, the inverse population is established between the upper state and lower state. In our case, they are $C^3\pi_u$ and $B^3\pi_g$ state. In fact, this transition we studied here is the operation wavelength of $N_2$ laser.

However, the gain length is expected to be related to the fluorescence lifetime around several ns. The relative short lifetime of upper state means that of the inversion can only be obtained during the effective lifetimes of the C-state. To estimate the lifetime of the upper state in our current experimental condition, the temporal profile of the fluorescence signal is measured with PMT by collecting the fluorescence signal in the right angle. By comparing with the measurement for the laser scattering, it is found that the lifetime of $C^3\pi_u$ is around several ns. In the experiment with external lens to focus the laser beam, the maximum filament length is around 20 cm which correspond to less than 1 ns traveling time for the light. When the fluorescence goes through the filament, most of the excited $N_2$ molecules remain in the upper state and the inverse population remains between $C^3\pi_u$ and $B^3\pi_g$ state. Thus the spontaneous emission is amplified. When the laser pulses propagate in the air without passing through any focusing lens, the filament length is rather long (about several meters). The effective amplification is reduced and this is what we have observed. On the other hand, the experiment and theoretical results showed the intensity distribution along the filaments oscillates gradually because of the repetitive Kerr focusing and plasma defocusing effects that lead to a dynamic balance resulting in the perceived filament. This will also result in the effective gain effect reductions since the nonlinear fluorescence is highly related to the intensity inside the filament.

It is interesting to note that our observation shows that there is gain inside the emission from the $N_2$ ions. This is probably because the electron-ion recombination rate for the upper state $B^2\Sigma_u^+$ is slower than that for $X^2\Sigma_g^-$ state resulting in a population inversion between these two states.

The exponential variation of the fluorescence from $N_2$ molecules and ions with increasing filament length indicate the fluorescence has been amplified when propagating along the filament. Since the gain length is changed with different experimental setup, the gain coefficient is different from case to case. It is expected that in the forward direction, because of symmetry, the nitrogen fluorescence would also exhibit ASE type of gain. Thus, we can say that there is laser action in the filaments generated by an intense femtosecond Ti-sapphire laser pulse in air.

The existence of gain is particularly important for remote sensing application with intense ultra fast laser. It is expected that the fluorescence from other molecules will undergo amplification during propagating along the filament as well because the molecules would be ionized first through MPI and then decay through all allowed excited states after e-ion recombination. Those radiated excited states are inverted with respect to the lower states since they are populated from the continuum down. Therefore in the direction opposite to that of the transmitted pulse, the fluorescence will be much stronger than the other directions: thus a higher sensitivity is expected. Indeed, this is a universal phenomenon in all gases which exhibit fluorescence in the filament of an intense femtosecond laser pulse.

A feasibility study was carried out on measuring the fluorescence spectra of atmospheric pollutants in our laboratory environment. The samples we chose include the following molecules: $N_2$, CO, $CO_2$, Ethylene, 1-Butene and N-Butane. All molecular spectra are free of the interference of plasma continuum because the plasma density is very low in the filament, resulting that the peaks in the spectrum are clearly resolved. Even for molecules with similar structures (such as CO and $CO_2$ or 1-Butene and N-Butane), the spectra clearly showed us the difference either on the peak positions or the intensity ratio between different peaks. This is due to the different nonlinear interactions between those molecules and the laser pulses. The minimum detection sensitivity of this technique was also evaluated by measuring the characteristic spectra from the mixture of these gases with air at different partial pressures. The sensitivity of this technique could reach several tens to several hundreds of ppb (parts per billion) level in volume concentration.

The feasibility of detecting fluorescence at a long distance was checked by measuring one of the fluorescence lines from $N_2$ in air using the LIDAR technique as well. We are able to detect the signal from many tens of meters away. Were it not for the confine of the laboratory, this distance can still be much longer. This proves that long distance fluorescence is measurable.

In order to measure a signal over a desired time interval corresponding to a desired range, a shutter is used on the detector. The shutter is set to open after a fixed amount of time, for example 500 ns. In order to obtain a signal received between 500 ns and 700 ns, the spectra of the signal captured after 500 ns and the spectra of a signal captured after 700 ns are subtracted from one another in order to obtain a spectra for a signal from 500 ns to 700 ns. This can be done using a gated detector.

It is also possible to detect the amplified spontaneous fluorescence signals in the same direction as that of the transmitted pulse by placing a detector in front of the source. In this case, the detector senses the amplified spontaneous fluorescence signals that are maintained in the waveguide formed by the filament and are moving forwards. There is a possibility that the source burns a hole through the detector when the detector is placed on a same axis as the source and receives forward moving amplification signals because it also receives the original femtosecond pulse output from the source. Therefore, it may be necessary to replace the detector after a certain amount of transmissions and detections. Receiving optics can be designed to reduce the damage to the detector. Such receiving optics are known to a person skilled in the art.

In short, we prove that the nonlinear fluorescence spectra from different kinds of molecules interacting with intense femtosecond laser field constitute the distinct evidence of fingerprints of pollutants, and sub-ppm (part per million) level of detection sensitivity can be achieved. The proposed technique is based upon the most advanced modern femtosecond laser technology; it is unique and powerful in the sense that one laser would be able to sense all molecular pollutants simultaneously. No other type of laser could do so. The application of this technique could lead to the establishment and enhancement of activities in photonics industries and government organizations interested in atmospheric pollution monitoring. In particular, this technique can be applied to monitoring chemical/biological pollutants in the atmosphere spread over by terrorist groups.

Figure 5:
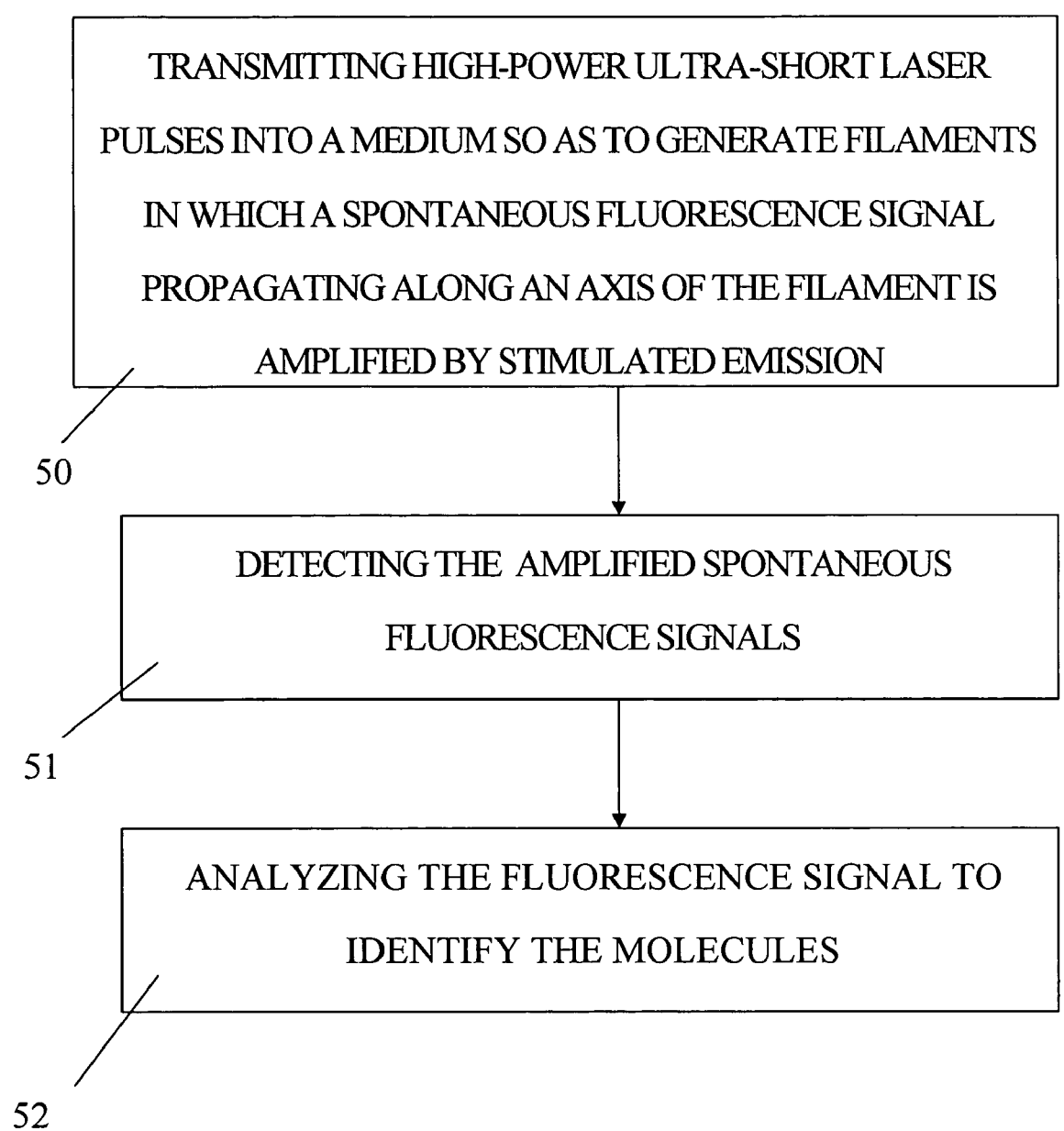
FIG. 5 is a flow chart of the method according to the invention.

FIG. 5 is a flowchart showing the method according to the present invention. The first step is to transmit a high-power, ultra-short laser pulse into a transparent medium so as to generate filaments in which a spontaneous fluorescence signal propagating along the axis of said filament is amplified by stimulated emission 50. When transmitting femtosecond laser pulses into the atmosphere, or any other substantially transparent medium, a weak plasma column is formed and serves as an amplifying waveguide to the spontaneous emission fluorescence signals. The amplified spontaneous fluorescence signals are then detected 51 and analyzed to identify molecules from the unique characteristics in their fluorescence spectrum 52.

Preferably, the transmitting is done using a femtosecond laser, and more specifically, a terawatt femtosecond Ti:sapphire laser system. Also preferably, the detected signals are in a direction opposite that of the transmitted pulse and received by the detector, which is placed at the same location as the source. As an additional feature, a trigger-and-delay electronics device is present in order to capture signals from a certain distance from the source and the detector is gated. For example, when the medium of transmission is air, the time at which the fluorescence spectra are acquired determines at what height the detection is being done. The longer the delay between the laser pulse and the acquisition of the spectrum, the higher the signal is coming from.

The transmission medium can be air, water, or any other medium that is substantially transparent and in which a filament can be formed.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method for identifying at least one molecule in a substantially transparent medium, the method comprising:
    transmitting high-power, ultra-short laser pulses into the medium so as to generate filaments in which a spontaneous fluorescence signal propagating along an axis of said filament is amplified by stimulated emission;
    detecting said amplified spontaneous fluorescence signal; and
    analyzing said florescence signal to identify said molecule.

2. A method as claimed in claim 1, wherein said amplified spontaneous fluorescence signals are detected along a direction opposite to said transmitted laser pulses.

3. A method as claimed in claim 2, wherein said detecting comprises measuring said signal over a desired time interval corresponding to a desired range.

4. A method as claimed in claim 3, wherein said detecting comprises using a shutter to select said desired time interval within said desired range by setting said shutter to open after a predetermined time period.

5. A method as claimed in claim 1, wherein said transmitting comprises transmitting femtosecond laser pulses.

6. A method as claimed in claim 1, wherein said transmitting comprises transmitting using a terawatt femtosecond Ti-sapphire laser system.

7. A method as claimed in claim 1, wherein said transmitting comprises transmitting said laser pulses from ground to sky.

8. A method as claimed in claim 1, wherein said at least one molecule is nitrogen and said substantially transparent medium is the atmosphere.

9. A method as claimed in claim 1, wherein said transmitting comprises transmitting said laser pulses into the atmosphere to perform atmospheric analysis.

10. A method as claimed in claim 1, wherein said at least one molecule is selected from a group consisting of carbon monoxide, carbon dioxide, ethylene, and Butane.

* * * * *